United States Patent [19]

Renner et al.

[11] 4,230,851

[45] Oct. 28, 1980

[54] PROCESS FOR THE PRODUCTION OF 2-EQUIVALENT YELLOW COUPLERS

[75] Inventors: Günter Renner; Quirin Scheben, both of Cologne, Fed. Rep. of Germany

[73] Assignee: AGFA-Gevaert, A.G., Leverkusen, Fed. Rep. of Germany

[21] Appl. No.: 74,895

[22] Filed: Sep. 12, 1979

[30] Foreign Application Priority Data

Sep. 16, 1978 [DE] Fed. Rep. of Germany ....... 2840381

[51] Int. Cl.³ .................. C07D 253/04; C07D 239/88; C07D 233/64; C07D 473/08
[52] U.S. Cl. .................................... 544/183; 544/287; 544/255; 548/321; 548/305; 548/343; 260/556 B; 260/562 P; 260/326 A; 546/271

[58] Field of Search ....................... 544/183, 287, 255; 548/321, 305; 260/556 B, 562 P, 326 A; 546/312

[56] References Cited

U.S. PATENT DOCUMENTS

| | | | |
|---|---|---|---|
| 4,133,955 | 1/1979 | Renner | 544/183 |
| 4,138,557 | 2/1979 | Boie et al. | 544/183 |

*Primary Examiner*—John M. Ford
*Attorney, Agent, or Firm*—Connolly & Hutz

[57] ABSTRACT

α-Acylacetamide 2-equivalent yellow couplers may be prepared by reacting α-halo-α-acyl-acetamides with phenols or NH-acidic organic compounds in the presence of a non-alkylatable bicyclic nitrogen-containing base, such as 1,5-diazabicyclo[4,3,0]non-5-ene or 1,8-diazabicyclo[5,4,0]-undec-7-ene.

5 Claims, No Drawings

PROCESS FOR THE PRODUCTION OF 2-EQUIVALENT YELLOW COUPLERS

This invention relates to a new process for the production of 2-equivalent yellow couplers.

In subtractive three-color silver halide photography, it is standard practice to use color couplers which, during the color development of the exposed photographic material, couple with the oxidized developer substance, particularly an aromatic compound containing primary amino groups, to form a cyan, magenta and yellow dye image. Open-chain ketomethylene compounds (cf.Mees & James "The Theory of the Photographic Process", 3rd Edition, 1966, pages 388–389), preferably acyl acetamides, for example acyl acetanilides, are used for producing the yellow dye image.

It is also known to use yellow couplers in which the methylene group is unsubstituted, so that four equivalents of silver halide have to be developed to produce one molecule of dye, and yellow couplers in which the methylene group carries a substituent which is split off during color development so that only two equivalents of silver halide have to be developed for forming one molecule of dye. The former compounds are known as "4-equivalent couplers" and the latter as "2-equivalent couplers".

The main advantages of 2-equivalent color couplers are well known. They require only half as much silver halide as 4-equivalent couplers, so that less silver halide is required in the production of the photographic materials and thinner silver halide emulsion layers can be used, resulting in improved resolution and image definition.

Thus, French Pat. No. 1,411,384, for example, describes 2-equivalent yellow couplers, the active methylene group of which carries an aroxy group, particularly a phenoxy substituent. These 2-equivalent couplers are produced by reacting the corresponding coupler containing a chlorine atom as substituent in the coupling position (in the active methylene group), with phenols in the presence of triethylamine as basic condensation agent in acetonitrile as solvent. However, this process leads to the formation of numerous secondary products, so that the phenoxy-substituted coupler is difficult to isolate and poor yields are obtained.

Other known 2-equivalent yellow couplers which contain a heterocyclic group attached through nitrogen in the coupling position (cf. for example German Offenlegungsschrift Nos. 2 318 807, 2 329 587 and 2 363 675) are produced by reacting the corresponding coupler substituted with chlorine or bromine on the methylene group with a suitable heterocyclic group in an aprotic solvent, for example in dimethyl formamide, hexamethyl phosphoric acid triamide or dimethyl sulfoxide, in the presence of a base, for example an aliphatic amine, such as triethylamine or tetramethyl guanidine, a basic heterocyclic compound, such as pyridine or 1,4-diazabicyclo[2,2,2]octane (DABCO), or an alkali salt of alcohols, such as sodium methylate. Unfortunately, these processes are also accompanied by undesirable secondary reactions.

The object of the present invention is to produce 2-equivalent yellow coupler compounds in better yields with as small a number of secondary products as possible being formed.

It has now been found that 2-equivalent acyl acetamide yellow couplers, i.e. acyl acetamides substituted in the α-position by an organic leaving group, can be obtained in high yields and in highly pure form by reacting α-halogen acyl acetamide couplers, i.e. acyl acetamide couplers containing a halogen atom, particularly a chlorine atom or a bromine atom, in the coupling position (in the methylene group), with an organic compound supplying the leaving group, preferably in an aprotic solvent using bicyclic heterocyclic bases which cannot be alkylated as basic condensation agents.

The non-alkylatable bicyclic nitrogen-containing bases used in accordance with the invention are bicyclic organic compounds consisting essentially of carbon, hydrogen and nitrogen atoms and containing from 6 to 14 carbon atoms and at least 1, preferably at least 2, nitrogen atoms. The nitrogen atoms are attached solely to carbon atoms through their free valences to form single bonds or unconjugated double bonds, so that it is possible to refer to them as tertiary amines. Examples of nonalkylatable bicyclic nitrogen-containing bases suitable for use in accordance with the invention are 1,5-diazabicyclo-[4,3,0]-non-5-ene (DBN) and 1,8-diazabicyclo-[5,4,0]-undec-7-ene (DBU).

By using a non-alkylatable bicyclic base as the basic condensation agent, it is possible to introduce into the coupling position of the yellow couplers a variety of organic substituents derived from organic compounds with varying acidity including phenols (of the type described for example in the above-mentioned French Patent) and NH-acid organic compounds, particularly heterocyclic compounds containing at least one acid NH-group in the ring (of the type described for example in the above-mentioned German Offenlegungsschriften), of which a few representative examples are given in Table I below:

TABLE I

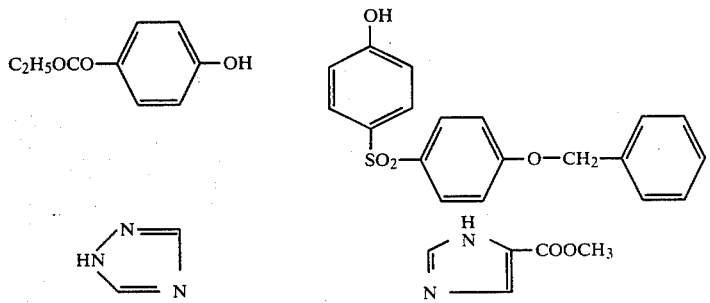

TABLE I-continued

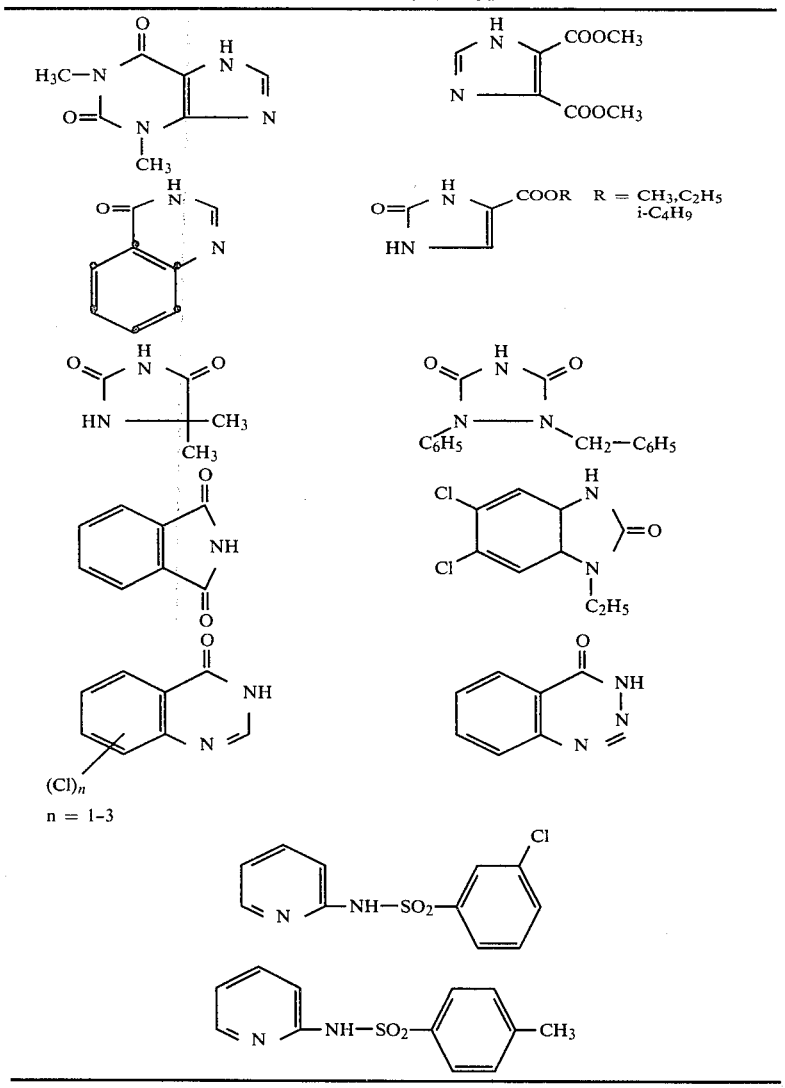

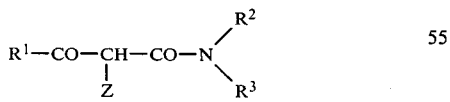

In the process according to the invention substitution is highly selective so that only few secondary products are formed and the yields obtained are higher than in conventional processes. The reaction products isolated have a high degree of purity.

The α-halogen acyl acetamides reacted in accordance with the invention are in particular α-halogen-α-acyl acetamides corresponding to the general formula $$R^1-CO-CH-CO-N\diagdown_{R^3}^{R^2}$$
$$\quad\quad\quad\quad |$$
$$\quad\quad\quad\quad Z$$

in which $R^1$, $R^2$ and $R^3$ represent groups of the type normally present in acyl acetamide yellow couplers and Z is a halogen atom, particularly a chlorine atom or a bromine atom.

$R^1$, $R^2$ and $R^3$ represent any of the groups normally present in acyl acetamide yellow couplers, for example in color couplers of the type described in U.S. Pat. Nos. 3,056,675, 3,369,899, 3,393,040, 3,393,041, 3,409,439, 3,619,190, 3,645,742, 3,660,095 and 3,725,072; in Belgian Pat. No. 717 841 and in German Offenlegungsschriften Nos. 2 002 378, 2 114 576, 2 114 577 and 2 114 578. In particular, $R^1$, $R^2$ and $R^3$ may represent one of the following groups:

$R^1$ a straight-chain or branched alkyl group preferably containing from 1 to 18 carbon atoms which, in the case of a secondary or tertiary alkyl group, is preferably attached to the carbonyl group through the secondary or tertiary carbon atom, an alkoxyalkyl group, an aroxyalkyl group, a bicycloalkyl group, a heterocycle or an aryl group, preferably a phenyl group which may contain one or more substituents such as, for example, $C_1$—$C_{18}$-alkyl, $C_1$—$C_{18}$-alkoxy, aralkyl, aryl, aroxy, sulfo, carboxy, halogen such as chlorine, bromine and fluorine, acyl, acyloxy, acylamino or amino;

$R^2$ hydrogen or a $C_1$—$C_5$-alkyl group, such as methyl, and $R^3$ $C_1$—$C_{18}$—alkyl, a heterocyclic group such as 2-thiazolyl, or preferably aryl, such as phenyl, which may be substituted by one or more substituents such as, for example, $C_1$—$C_{18}$-alkyl, $C_1$—$C_{18}$-alkoxy, halogen, such as chlorine, bromine and fluorine, sulfo, carboxy, aryl, aralkyl, aroxy, acyl, acyloxy, acylamino or amino.

Where reference is made above in the definition of $R^1$ and $R^3$ to acyl radicals, these acyl radicals are derived from organic acids, such as aliphatic or aromatic carboxylic or sulfonic acids, including carbonic acid semiesters, carbamic acids and sulfamic acids, of which the last two may be substituted on the nitrogen atom by an alkyl, aryl, aralkyl or a heterocycle.

The 2-equivalent yellow couplers produced by the process according to the invention are of course preferably derived from known 4-equivalent color couplers with excellent properties in regard to the absorption and stability of the dyes formed during color development.

It is preferred to use pivaloyl acetanilides and benzoyl acetanilides, particularly o-alkoxy benzoyl acetanilides, which may contain in the aniline radical from 1 to 3 substituents of the above-mentioned type, preferably in the 2-, 4- and 5-positions.

In the process according to the invention, the couplers containing a chlorine- or bromine-substituted methylene group and the compounds supplying the leaving group are generally used in equimolar quantities, although the compounds supplying the leaving group may also be used in excess.

The non-alkylatable bicyclic nitrogen-containing base may be used in equimolar quantities in relation to the compounds supplying the leaving group. However, it is preferred to use the non-alkylatable bicyclic base and the compound supplying the leaving group in a molar ratio of two or more.

In general, the substitution reaction is carried out by heating the reactants to between 40 and 100° C. and preferably to between 50 and 80° C. in a suitable solvent, such as acetonitrile, 2-butanone, acetone, dimethyl formamide, dimethyl acetamide, N-methyl pyrrolidone, hexamethyl phosphoric acid triamide (HEMPA) and the like. The quantity in which the solvent is used is not critical and is governed by the solubility of the reactants therein.

The reaction is best carried out by initially introducing the nucleophilic reactant, i.e. the compound supplying the leaving group, together with the nonalkylatable bicyclic nitrogen-containing base dissolved in an aprotic, preferably dipolar solvent at the reaction temperature and adding the α-halogen substituted β-ketoacetanilide, optionally dissolved in the same way.

However, the above-mentioned non-alkylatable bicyclic nitrogen-containing bases may also be slowly added dropwise to a solution of the compound supplying the leaving group and the yellow coupler halogenated in the α-position. Similarly 4-equivalent couplers unsubstituted in the coupling position may be reacted to form the required 2-equivalent couplers by the methods described in German Offenlegungsschrift No. 2 545 756 using the bicyclic heterocyclic bases employed in accordance with the invention, in which case the coupler halogenated in the α-position presumably occurs solely as an intermediate product, but is not isolated.

The reaction conditions (reaction temperature) are preferably selected in such a way that the velocity of the reaction of the nucleophilic reactant with the coupler halogenated in the α-position is as high as possible. Since a prolonged residence time of the halogenated coupler in the alkaline reaction medium is frequently a disadvantage, it is important for the two reactants to react quickly with one another.

The 2-equivalent yellow coupler produced by the process according to the invention may be isolated from the reaction medium in the usual way by pouring the reaction mixture into water, acetic acid, dilute sulfuric acid or dilute hydrochloric acid and recrystallising it, resulting in the formation of a highly pure color coupler. With some compounds, re-crystallisation is preceded by an extraction step.

Representative example of 2-equivalent color couplers obtainable by the process according to the invention are shown in Table II below. The process by which they are produced is illustrated by the Synthesis Examples given further below.

TABLE II

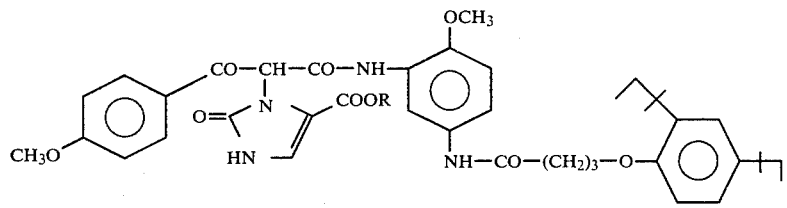

1. R = CH₃    mp = 185°-87° C.    yield 76%
2. C₂H₅      = 154°-57° C.       yield 73%
3. C₄H₉      = 121°-25° C.       yield 72%
4.

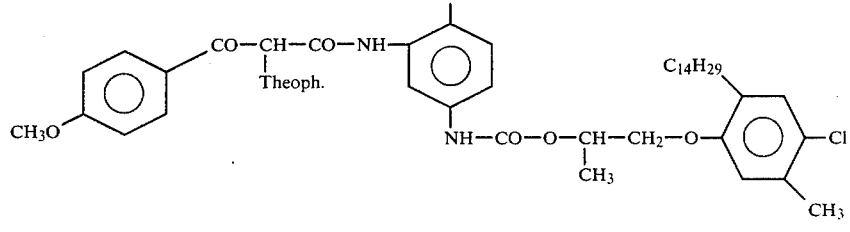

mp = 83° C.    yield 67%

TABLE II-continued
5. 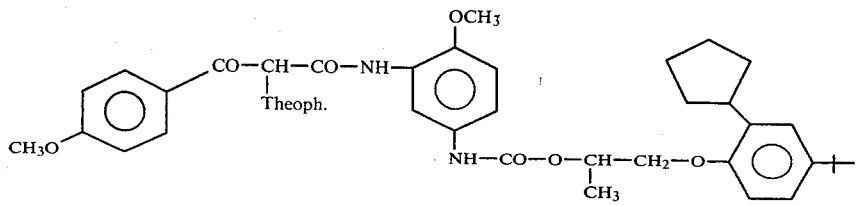
mp = 165°-67° C.  yield 77%
6. 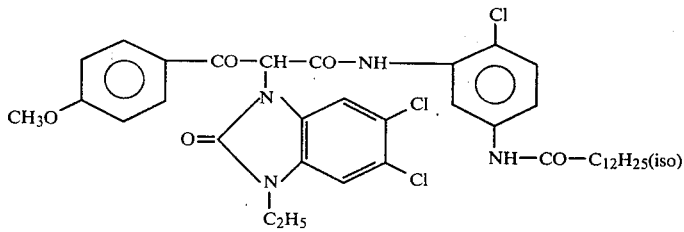
mp = 160°-62° C.  yield 63%
7. 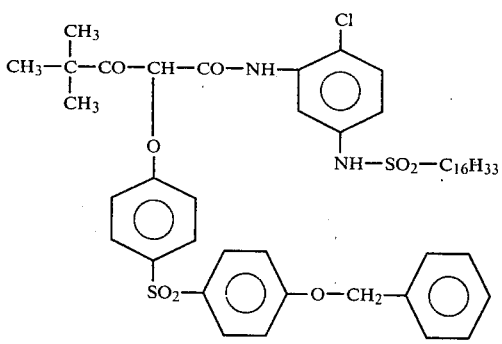
mp = 92°-94° C.  yield 69%
8. 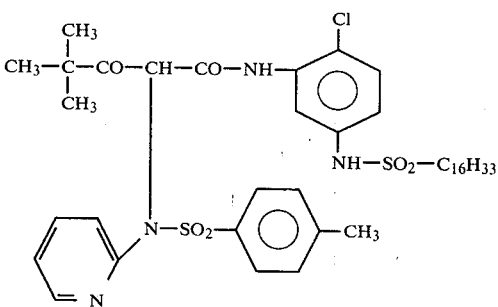
mp = 123°-125° C.  yield 61%
9. 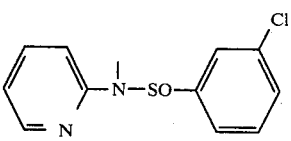
mp = 110°-12° C.  yield 63%
10. 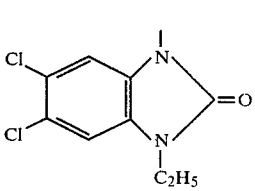
mp = 90°-92° C.  yield 70%

TABLE II-continued
11. 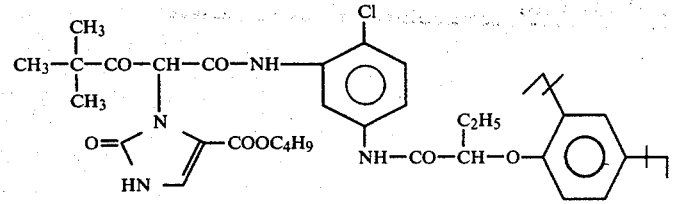
mp = 163°–65° C.   yield 53%
12. 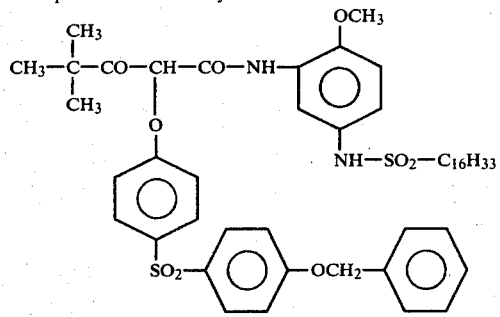
mp = 129°–30° C.   yield 64%
13. 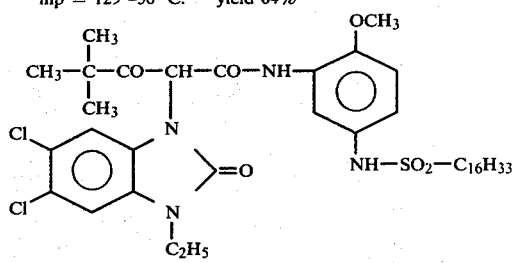
mp = 156°–58° C.   yield 81%
14. 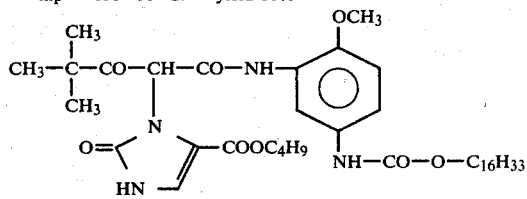
mp = 127°–129° C.   yield 84%
15. 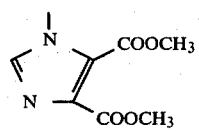
mp = 110°–113° C.   yield 77%
16. 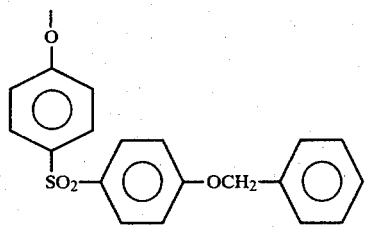
mp = 134°–36° C.   yield 75%
17. 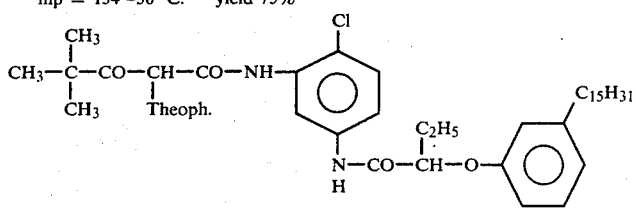
oil   yield 75%

TABLE II-continued
18. 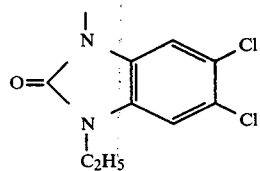
mp = 70°-72° C.   yield 53%
19. 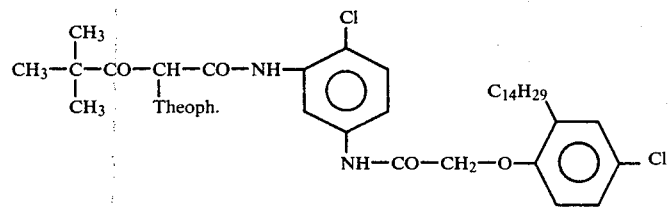
oil   yield 82%
20. 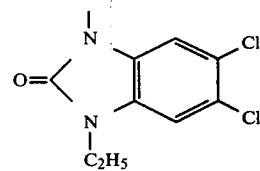
mp = 128°-29° C.   yield 77%
21. 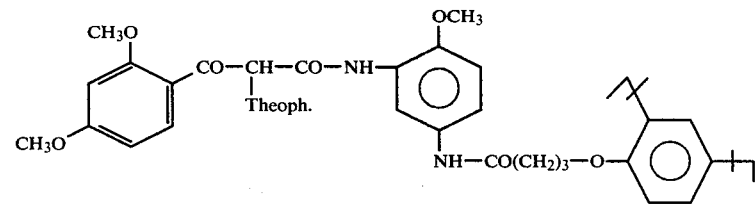
mp = 108°-111° C.   yield 62%
22. 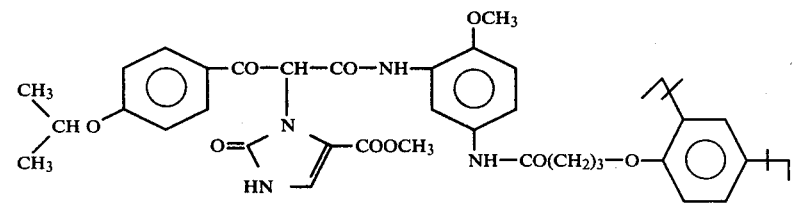
mp = 233°-36° C.   yield 73%
23. 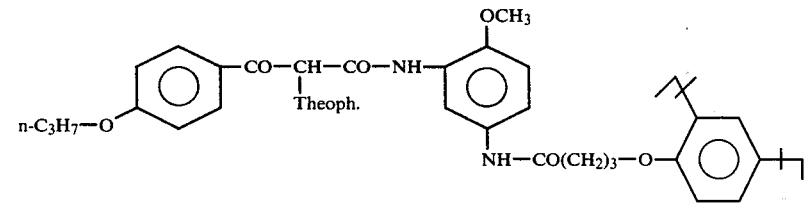
mp = 148°-50° C.   yield 63%
24. 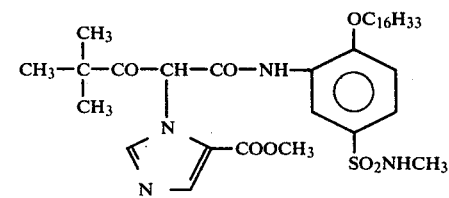
mp = 69°-72° C.   yield 86%

TABLE II-continued
25. 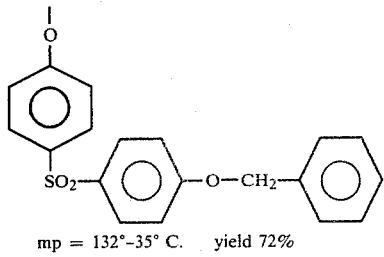
mp = 132°-35° C.   yield 72%
26. 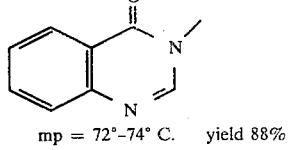
mp = 72°-74° C.   yield 88%
27. 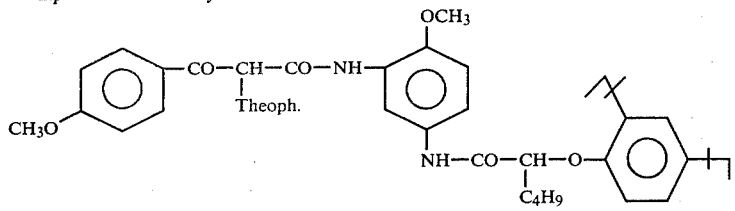
mp = 178°-81° C.   yield 86%
28. 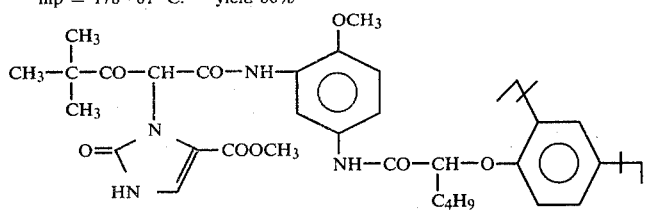
F = 200°-203° C.   yield 71%
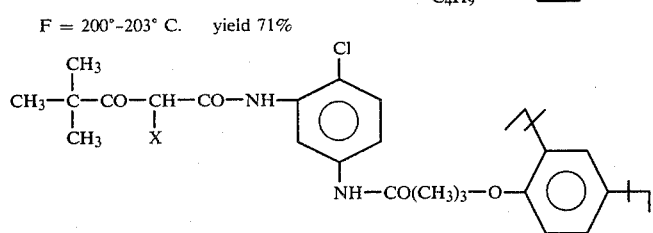
29. 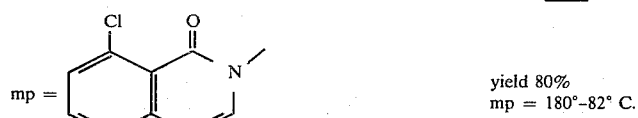
mp =   yield 80%
mp = 180°-82° C.
30. 
yield 76%
mp = 182°-85° C.
31. 
yield 67%
mp = 187°-90° C.
32. 
yield 54%
mp = 108°-110° C.

TABLE II-continued

33. 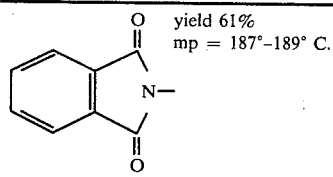 yield 61%
mp = 187°–189° C.

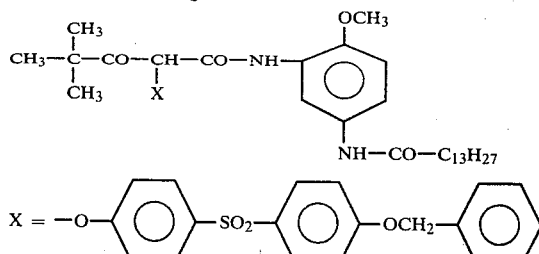

34. X = 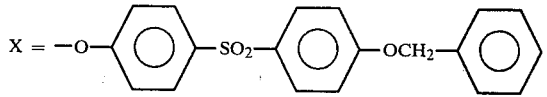
mp = 110°–12° C. yield 68%
35. X = Theoph.
mp = 170°–73° C. yield 71%
36. X = 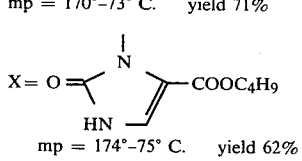
mp = 174°–75° C. yield 62%
37. X = 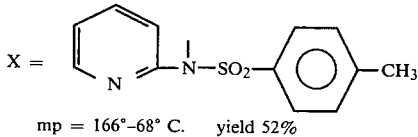
mp = 166°–68° C. yield 52%

Theoph. = Theophyllin

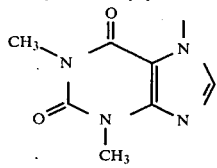

SYNTHESIS EXAMPLES

Coupler 13

α-(5,5-dichloro-3-ethylbenzimidazol-2-on-1-yl)-2-methoxy-5-cetyl sulfonamide pivaloyl acetanilide 41 g of α-pivaloyl-α-chloro-2-methoxy-5-cetyl sulfonamido acetanilide and 21 g of 5,6-dichloro-3-ethyl benzimidazolone were dissolved in 300 ml of dimethyl acetamide. 30 ml of diazabicycloundecene (DBU) were then added dropwise at 30° to 40° C. The reaction product was precipitated in ice/hydrochloric acid and recrystallised from alcohol. The required 2-equivalent coupler 13 was obtained in a yield of 45.2 g.

Coupler 11

2-Chloro-5-(α-2,4-di-tert.-amyl-phenoxy-butyramido)-α-(5-butoxy-carbonyl-imidazolin-2-on-1-yl)-α-pivaloyl acetanilide The procedure was the same as for the synthesis of coupler 13, using 30 g of 2,α-dichloro-5-(α2,4-di-tert.-amyl-phenoxy-butyramido)-α-pivaloyl acetanilide, 10.5 g of 4-butoxycarbonyl-imidazolin-2-one and 17 g of diazabicyclononene (DBN). Coupler 11 was obtained in a yield of 53%.

Coupler 27

2-Methoxy-5-(α-2,4-di-tert.-pentylphenoxy-caprylamido)α-4,6-dimethyl-5,7-dioxo-4,5,6,7-tetrahydro-1-imidaxolo-[4,5-d]-pyrimidinyl)-α-(4-methoxybenzoyl)acetanilide 10 g of theophylline were dissolved in 100 ml of HEMPA with 19 g of DBU. A solution of 34 g of α-(4-methoxybenxoyl)-α-chloro-2-methoxy-5-(α-2,4-di-tert.-pentyl-phenoxy-caprylamido)-acetaniline in 50 ml of HEMPA was then added at 60° C. After acid precipitation, the product was recrystallised from alcohol. The required coupler 27 was obtained in a yield of 86%.

COMPARISON TESTS

1. Using the bases listed in the following Table, the coupler 4 was produced from the corresponding coupler chlorinated in the α-position, 2, α-dichloro-5-[2-(4-chloro-5-methyl-2-tetradecyl phenoxy)-isopropoxycarbonylamino]-α-(4-methoxybenxoyl)-acetanilide, and theophylline by the following method:

100 ml of dimethylacetamide and 0.2 mole of base were added to 0.12 mole of theophylline. After heating to 70° C., 0.1 mole of the chlorinated coupler was added, followed by stirring in water/ice/hydrochloric acid, filtration under suction and washing with water.

The dry crude product was dissolved in and allowed to crystallise from acetonitrile.

The yield obtained is shown in Table III:

TABLE III

| Base | Yield [g] | [%] |
|---|---|---|
| NaOH | 37 | 40.9 |
| NaOCH$_3$ | 36 | 39.8 |
| Tetramethyl guanidine (TMG) | 44 | 48.6 |
| LiOH | 39 | 43.1 |
| DBU | 62 | 68.5 |
| tert.-C$_4$H$_9$—OK | 39 | 43.1 |

2. Repetition of the test using acetonitrile as solvent gave the following results:

| Base | Yield [g] | [%] |
|---|---|---|
| NaOCH$_3$ | 32 | 35.4 |
| TMG | 37 | 40.9 |
| DBU | 43 | 47.5 |

3. Results comparable with those obtained in test 1 were observed with HEMPA as solvent.

4. Production of coupler 24:
2-hexadecoxy-α-(5-methoxycarbonyl-imidazolyl)-5-(N-methylsulfamoyl)-α-pivaloyl acetanilide:

The procedure was as described for test 1, except that the compound supplying the leaving group (4-methoxycarbonyl-imidazole) was used in an excess of only 10% and the 2-equivalent coupler chlorinated in the α-position was added at 50° C.

| Base | Solvent | Yield [%] |
|---|---|---|
| TMG | dimethylacetamide | 69 |
| NaOCH$_3$ | acetonitrile | 64 |
| DBU | dimethylacetamide | 86 |

We claim:

1. The process for the production of a 2-equivalent α-acylacetamide yellow coupler substituted in the α-position with an organic substituent selected from the group consisting of phenoxy groups and groups derived from NH acidic organic compounds by removal of the acidic hydrogen atom in which process a 2-equivalent α-halo-α-acylacetamide yellow coupler is reacted with a compound selected from the group consisting of phenols and NH-acidic organic compounds in the presence of a basic condensing agent, in which process the improvement comprises using as basic condensing agent a non-alkylatable bicyclic nitrogen-containing base containing from 6 to 14 carbon atoms and at least 2 nitrogen atoms.

2. Process as claimed in claim 1 in which 1,5-diazabicyclo-[4,3,0]-non-5-ene (DBN) or 1,8-diazabicyclo[5,4,0]-undec-7-ene (DBU) is used as the basic condensation agent.

3. Process as claimed in claim 1 in which the reaction is carried out in an aprotic, dipolar solvent.

4. Process as claimed in claim 1 in which an α-halogen-α-pivaloyl acetanilide or an α-halogen-αbenzoyl acetanalide is used as the α-halogen-α-acylacetamide.

5. Process as claimed in claim 1 in which the α-halogen-α-acylacetamide corresponds to the formula

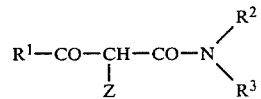

in which
Z represents halogen and
R$^1$, represents alkyl, a heterocycle or aryl,
R$^2$ represents hydrogen or C$_1$—C$_5$-alkyl and
R$^3$ represents alkyl, a heterocyclic group, aryl or substituted aryl.

* * * * *